(12) United States Patent
Hyland et al.

(10) Patent No.: US 11,749,376 B2
(45) Date of Patent: Sep. 5, 2023

(54) SYSTEMS AND METHODS FOR IDENTIFYING SEQUENCE VARIATION ASSOCIATED WITH GENETIC DISEASES

(71) Applicant: LIFE TECHNOLOGIES CORPORATION, Carlsbad, CA (US)

(72) Inventors: Fiona Hyland, San Mateo, CA (US); Heinz Breu, Palo Alto, CA (US)

(73) Assignee: LIFE TECHNOLOGIES CORPORATION, Carlsbad, CA (US)

(*) Notice: Subject to any disclaimer, the term of this patent is extended or adjusted under 35 U.S.C. 154(b) by 971 days.

(21) Appl. No.: 16/434,677

(22) Filed: Jun. 7, 2019

(65) Prior Publication Data

US 2020/0027525 A1    Jan. 23, 2020

Related U.S. Application Data

(62) Division of application No. 14/024,878, filed on Sep. 12, 2013, now Pat. No. 10,347,360.

(60) Provisional application No. 61/821,563, filed on May 9, 2013, provisional application No. 61/701,009, filed on Sep. 14, 2012.

(51) Int. Cl.
| | | |
|---|---|---|
| *G01N 33/48* | (2006.01) | |
| *G01N 33/50* | (2006.01) | |
| *G16B 20/20* | (2019.01) | |
| *G16B 20/00* | (2019.01) | |

(52) U.S. Cl.
CPC ............ *G16B 20/20* (2019.02); *G16B 20/00* (2019.02)

(58) Field of Classification Search
CPC .................................................... G16B 20/00
See application file for complete search history.

(56) References Cited

U.S. PATENT DOCUMENTS

| | | |
|---|---|---|
| 10,347,360 B2 | 7/2019 | Hyland et al. |
| 2008/0228703 A1 | 9/2008 | Kenedy et al. |
| 2009/0026082 A1 | 1/2009 | Rothberg et al. |
| 2009/0127589 A1 | 5/2009 | Rothberg et al. |
| 2009/0325145 A1 | 12/2009 | Sablon et al. |
| 2010/0137143 A1 | 6/2010 | Rothberg et al. |
| 2010/0197507 A1 | 8/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |

FOREIGN PATENT DOCUMENTS

| | | | |
|---|---|---|---|
| WO | 2006084131 A2 | 8/2006 | |
| WO | WO-2009126290 A2 * | 10/2009 | ........... A61K 47/545 |
| WO | 2012044847 A1 | 4/2012 | |

OTHER PUBLICATIONS

Craig et al. Ordering of cosmid clones covering the Herpes simplex virus type I (HSV-I) genome: a test case for fingerprint hybridisation. Nucleic Acids Research, vol. 18, pp. 2653-2660. (Year: 1990).*
Flaquer et al. The human pseudoautosomal regions: a review for genetic epidemiologists. European Journal of Human Genetics, vol. 16, pp. 771-779. (Year: 2008).*
Fuller et al. The challenges of sequencing by synthesis. Nature Biotechnology, vol. 27, pp. 1013-1023. (Year: 2009).*
Need et al. Clinical application of exome sequencing in undiagnosed genetic conditions. Journal of Medical Genetics, May 11, 2012, 9 pages.*
Marks JW, ed. Medical definition of compound heterozygote, Jun. 3, 2021, 2 pages; obtained online from www.medicinenet.com on Apr. 28, 2022. (Year: 2022).*
Sambrook et al., "Molecular Cloning: a Laboratory Manual (Third ed.)", 2000, Cold Spring Harbor Laboratory.
Wang et al. ("ANNOVAR: functional annotation of genetic variants from high-throughput sequencing data" Nucleic Acids Research, 2010, vol. 38, No. 16, pp. 1-7).
Trapnell et al. ("How to map billions of short reads onto genomes", National Biotechnology, May 2009, 27(5), pp. 455-457).
Iossifov, I et al., "De Novo Gene Disruptions in Children on the Autistic Spectrum", Neuron, Call Press, vol. 74, No. 2, Apr. 9, 2012, 285-299.
Kamphans, T et al., "GeneTalk: an expert exchange platform for assessing rare sequence variants in personal genomes", Bioinformatics, vol. 28, No. 19, Jul. 23, 2012, 2515-2516.
O'Connell, J et al., "PedCheck: a Program for Identification of Genotype Incompatibilities in Linkage Analysis" American Journal of Human Genetics, American Society of Human Genetics, vol. 63, Jan. 1, 1998, 259-266.
PCT/US2013/059365, International Search Report and Written Opinion dated Dec. 6, 2013, 16 pages.
Wang, Y et al., "Exome Sequencing Identifies Compound Heterozygous Mutations in CYP4V2 in a Pedigree with Retinitis Pigmentosa", PLoS One, vol. 7, No. 5, e33673, May 2012, 7 pages.

* cited by examiner

*Primary Examiner* — Russell S Negin
(74) *Attorney, Agent, or Firm* — JONES ROBB, PLLC

(57) ABSTRACT

Systems and method for identifying variants associated with a genetic disease can include obtaining calls for a plurality of individuals for a list of variant positions. The calls can be compared to identify variants that are found in affected individuals and absent in non-affected individuals. Such variants can include loss of heterozygosity, trans-phased compound heterozygotes, increased frequency mitochondrial variants, homozygous recessive variants, de novo variants, sex-linked variants, and combinations thereof.

13 Claims, 8 Drawing Sheets

SYSTEMS AND METHODS FOR IDENTIFYING SEQUENCE VARIATION ASSOCIATED WITH GENETIC DISEASES

CROSS-REFERENCE TO RELATED APPLICATIONS

This application is a divisional of U.S. patent application Ser. No. 14/024,878, filed Sep. 12, 2013, which claims priority pursuant to 35 U.S.C. § 119(e) to U.S. Provisional Patent Application Ser. No. 61/821,563, filed on May 9, 2013, and to U.S. Provisional Patent Application Ser. No. 61/701,009, filed on Sep. 14, 2012, each of which is incorporated by reference herein in its entirety.

FIELD

The present disclosure generally relates to the field of nucleic acid sequencing including systems and methods for identifying sequence variations associated with genetic diseases.

INTRODUCTION

Upon completion of the Human Genome Project, one focus of the sequencing industry has shifted to finding higher throughput and/or lower cost nucleic acid sequencing technologies, sometimes referred to as "next generation" sequencing (NGS) technologies. In making sequencing higher throughput and/or less expensive, one goal is to make the technology more accessible. This and other goals can be reached through the use of sequencing platforms and methods that provide sample preparation for samples of significant complexity, sequencing larger numbers of samples in parallel (for example through use of barcodes and multiplex analysis), and/or processing high volumes of information efficiently and completing the analysis in a timely manner. Various methods, such as, for example, sequencing by synthesis, sequencing by hybridization, and sequencing by ligation are evolving to meet these challenges.

Ultra-high throughput nucleic acid sequencing systems incorporating NGS technologies typically produce a large number of short sequence reads. Sequence processing methods should desirably assemble and/or map a large number of reads quickly and efficiently, such as to minimize use of computational resources. For example, data arising from sequencing of a mammalian genome can result in tens or hundreds of millions of reads that typically need to be assembled before they can be further analyzed to determine their biological, diagnostic and/or therapeutic relevance.

Exemplary applications of NGS technologies include, but are not limited to: genomic variant detection, such as insertions/deletions, copy number variations, single nucleotide polymorphisms, etc., genomic resequencing, gene expression analysis and genomic profiling.

Of particular interest are improved systems and methods for identifying variants that may be associated with genetic diseases. Recent advances in genotyping technologies have resulted in a better understanding of common human sequence variation, which has led to the identification of many novel genetic determinants of complex traits/diseases. Nevertheless, despite these successes, much of the genetic component of these traits/diseases remains incomplete. Although there may be many undiscovered polymorphisms associated with complex traits/diseases, the "common-disease common-variant" paradigm may not provide a complete picture.

From the foregoing it will be appreciated that a need exists for systems and methods that can detect genomic variants in homopolymer regions using nucleic acid sequencing data.

DRAWINGS

For a more complete understanding of the principles disclosed herein, and the advantages thereof, reference is now made to the following descriptions taken in conjunction with the accompanying drawings, in which.

Figure 1:
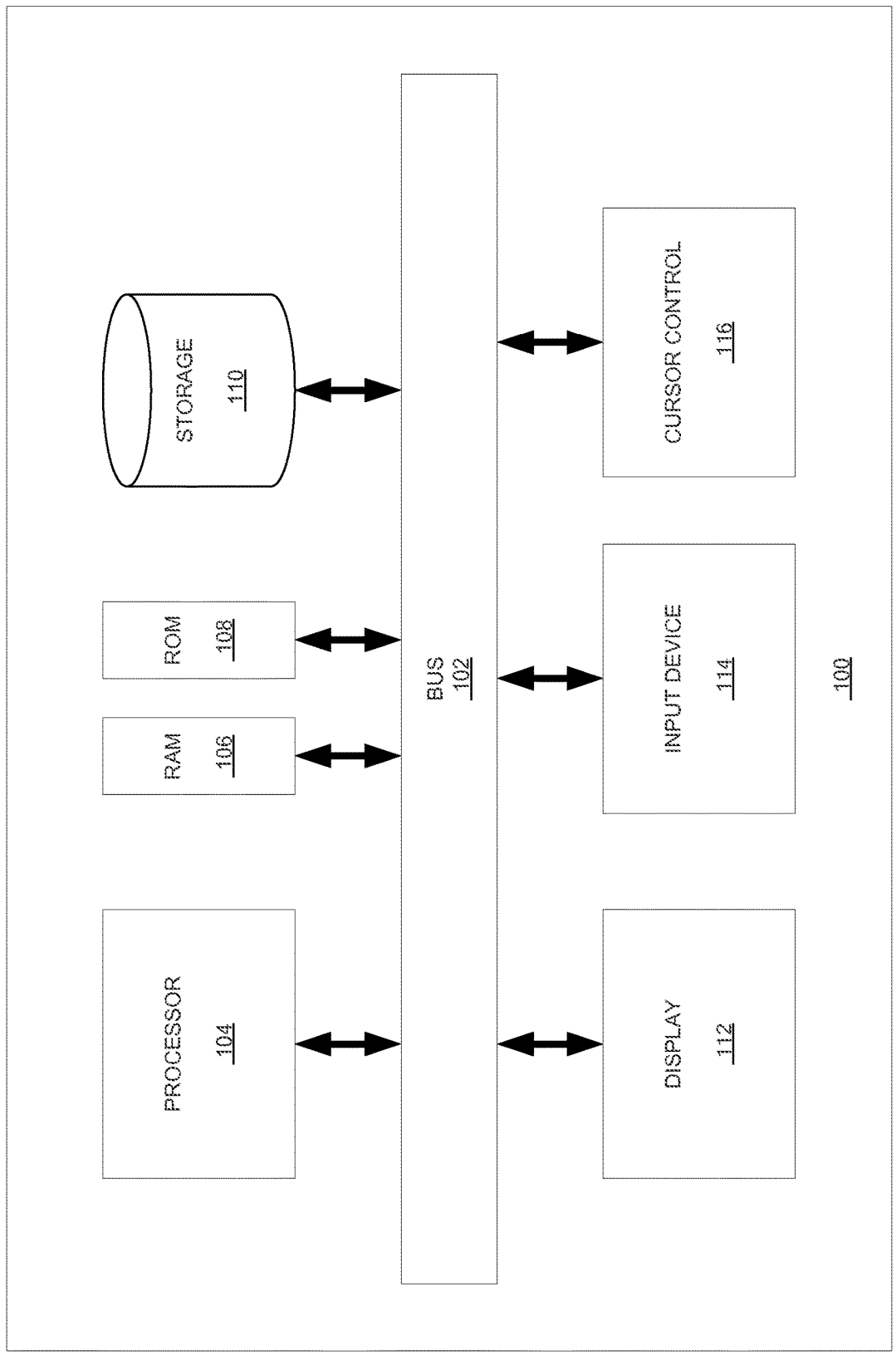
FIG. 1 is a block diagram that illustrates an exemplary computer system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for detecting variants are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, number of bases, coverage, etc. discussed in the present teachings, such that slight and insubstantial deviations are within the scope of the present teachings. In this application, the use of the singular includes the plural unless specifically stated otherwise. Also, the use of "comprise," "comprises," "comprising," "contain," "contains," "containing," "include," "includes," and "including" are not intended to be limiting. It is to be understood that both the foregoing general description and the following detailed description are exemplary and explanatory only and are not restrictive of the present teachings.

Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

As used herein, "a" or "an" also may refer to "at least one" or "one or more."

In various embodiments, a "system" sets forth a set of components, real or abstract, comprising a whole where each component interacts with or is related to at least one other component within the whole.

In various embodiments, a "biomolecule" may refer to any molecule that is produced by a biological organism, including large polymeric molecules such as proteins, polysaccharides, lipids, and nucleic acids (DNA and RNA) as well as small molecules such as primary metabolites, secondary metabolites, and other natural products.

In various embodiments, the phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the Personal Genome Machine (PGM) and Proton of Life Technologies Corp. provides massively parallel sequencing with enhanced accuracy. The PGM and Proton Systems and associated workflows, protocols, chemistries, etc. are described in more detail in U.S. Patent Application Publication No. 2009/0127589 and No. 2009/0026082, the entirety of each of these applications being incorporated herein by reference.

In various embodiments, the phrase "sequencing run" refers to any step or portion of a sequencing experiment performed to determine some information relating to at least one biomolecule (e.g., nucleic acid molecule).

In various embodiments, the phase "base space" refers to a representation of the sequence of nucleotides. The phase "flow space" refers to a representation of the incorporation event or non-incorporation event for a particular nucleotide flow. For example, flow space can be a series of zeros and ones representing a nucleotide incorporation event (a one, "1") or a non-incorporation event (a zero, "0") for that particular nucleotide flow. It should be understood that zeros and ones are convenient representations of a non-incorporation event and a nucleotide incorporation event; however, any other symbol or designation could be used alternatively to represent and/or identify these events and non-events.

In various embodiments, DNA (deoxyribonucleic acid) may be referred to as a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. In various embodiments, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

In various embodiments, a "polynucleotide," "nucleic acid," or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

In various embodiments, a "proband" refers to the individual under particular scrutiny. Typically, this will be the first member of an affected family to seek medical attention. A "family" refers to a group of individuals related to the proband by "blood or marriage." Genetic analysis of a family seeks to identify variant alleles that account for the phenotype of the proband. In general, some particular property of the phenotype will be of interest. An "affected" individual or family member refers to an individual that presents the property of interest. An "unaffected" individual or family member refers to an individual that does not present the property of interest.

Computer-Implemented System

FIG. 1 is a block diagram that illustrates an exemplary computer system 100, upon which embodiments of the present teachings may be implemented. In various embodiments, computer system 100 can include a bus 102 or other communication mechanism for communicating information, and a processor 104 coupled with bus 102 for processing information. In various embodiments, computer system 100 can also include a memory 106, which can be a random access memory (RAM) or other dynamic storage device, coupled to bus 102 for determining base calls, and instructions to be executed by processor 104. Memory 106 also can be used for storing temporary variables or other intermediate information during execution of instructions to be executed by processor 104. In various embodiments, computer system 100 can further include a read only memory (ROM) 108 or other static storage device coupled to bus 102 for storing static information and instructions for processor 104. A storage device 110, such as a magnetic disk or optical disk, can be provided and coupled to bus 102 for storing information and instructions.

In various embodiments, computer system 100 can be coupled via bus 102 to a display 112, such as a cathode ray tube (CRT) or liquid crystal display (LCD), for displaying information to a computer user. An input device 114, including alphanumeric and other keys, can be coupled to bus 102 for communicating information and command selections to processor 104. Another type of user input device is a cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results can be provided by computer system 100 in response to processor 104 executing one or more sequences of one or more instructions contained in memory 106. Such instructions can be read into memory 106 from another computer-readable medium, such as storage device 110. Execution of the sequences of instructions contained in memory 106 can cause processor 104 to perform the processes described herein. Alternatively hard-wired circuitry can be used in place of or in combination with software instructions to implement the present teachings. Thus implementations of the present teachings are not limited to any specific combination of hardware circuitry and software.

In various embodiments, the term "computer-readable medium" as used herein refers to any media that participates in providing instructions to processor 104 for execution. Such a medium can take many forms, including but not limited to, non-volatile media, volatile media, and transmission media. Examples of non-volatile media can include, but are not limited to, optical or magnetic disks, such as storage device 110. Examples of volatile media can include, but are not limited to, dynamic memory, such as memory 106. Examples of transmission media can include, but are not limited to, coaxial cables, copper wire, and fiber optics, including the wires that comprise bus 102.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

Nucleic Acid Sequencing Platforms

Nucleic acid sequence data can be generated using various techniques, platforms or technologies, including, but not limited to: capillary electrophoresis, microarrays, ligation-based systems, polymerase-based systems (such as Illumina HiSeq, MiSeq, and Genome Analyzer), hybridization-based systems, direct or indirect nucleotide identification systems, pyrosequencing (such as 454 Life Science GS FLX and GS Junior), ion- or pH-based detection systems (such as Ion Torrent), electronic signature-based systems (such as Oxford Nanopore GridION and MinION), etc.

Figure 2:
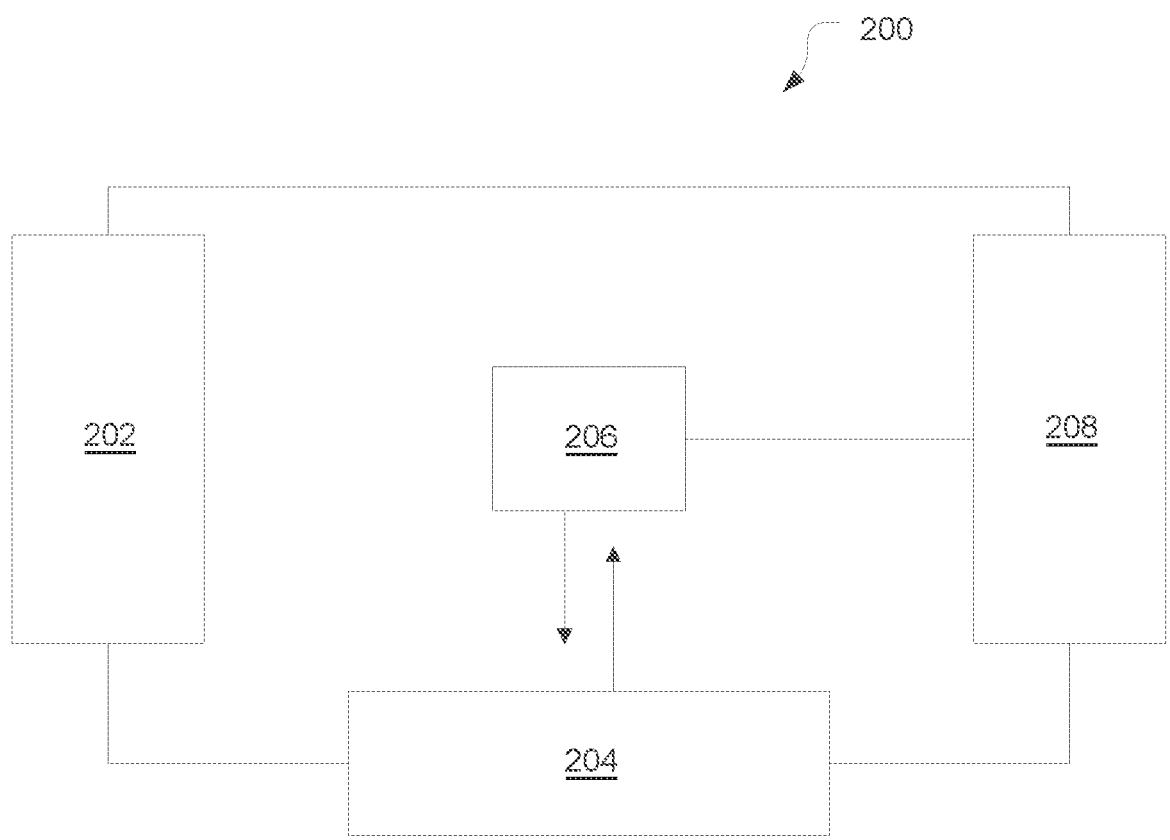
FIG. 2 is a schematic diagram of an exemplary system for reconstructing a nucleic acid sequence, in accordance with various embodiments.

Various embodiments of nucleic acid sequencing platforms, such as a nucleic acid sequencer, can include components as displayed in the block diagram of FIG. 2. According to various embodiments, sequencing instrument 200 can include a fluidic delivery and control unit 202, a sample processing unit 204, a signal detection unit 206, and a data acquisition, analysis and control unit 208. Various embodiments of instrumentation, reagents, libraries and methods used for next generation sequencing are described in U.S. Patent Application Publication No. 2009/0127589 and No. 2009/0026082 are incorporated herein by reference. Various embodiments of instrument 200 can provide for automated sequencing that can be used to gather sequence information from a plurality of sequences in parallel, such as substantially simultaneously.

In various embodiments, the fluidics delivery and control unit 202 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 204 can include a sample chamber, such as flow cell, a substrate, a micro-array, a multi-well tray, or the like. The sample processing unit 204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 206 can include an imaging or detection sensor. For example, the imaging or detection sensor can include a CCD, a CMOS, an ion or chemical sensor, such as an ion sensitive layer overlying a CMOS or FET, a current or voltage detector, or the like. The signal detection unit 206 can include an excitation system to cause a probe, such as a fluorescent dye, to emit a signal. The excitation system can include an illumination source, such as arc lamp, a laser, a light emitting diode (LED), or the like. In particular embodiments, the signal detection unit 206 can include optics for the transmission of light from an illumination source to the sample or from the sample to the imaging or detection sensor. Alternatively, the signal detection unit 206 may provide for electronic or non-photon based methods for detection and consequently not include an illumination source. In various embodiments, electronic-based signal detection may occur when a detectable signal or species is produced during a sequencing reaction. For example, a signal can be produced by the interaction of a released byproduct or moiety, such as a released ion, such as a hydrogen ion, interacting with an ion or chemical sensitive layer. In other embodiments a detectable signal may arise as a result of an enzymatic cascade such as used in pyrosequencing (see, for example, U.S. Patent Application Publication No. 2009/0325145, the entirety of which being incorporated herein by reference) where pyrophosphate is generated through base incorporation by a polymerase which further reacts with ATP sulfurylase to generate ATP in the presence of adenosine 5' phosphosulfate wherein the ATP generated may be consumed in a luciferase mediated reaction to generate a chemiluminescent signal. In another example, changes in an electrical current can be detected as a nucleic acid passes through a nanopore without the need for an illumination source.

In various embodiments, a data acquisition analysis and control unit 208 can monitor various system parameters. The system parameters can include temperature of various portions of instrument 200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 200 can be used to practice variety of sequencing methods including ligation-based methods, sequencing by synthesis, single molecule methods, nanopore sequencing, and other sequencing techniques.

In various embodiments, the sequencing instrument 200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 200 can obtain the sequence information from a single nucleic acid molecule or from a group of substantially identical nucleic acid molecules.

In various embodiments, sequencing instrument 200 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

Adaptor-Joining Methods:

In some embodiments, the present teachings are directed to methods for preparing a library of polynucleotide constructs which can include an adaptor-joining step. In some embodiments, a plurality of polynucleotide fragments can include at least two polynucleotide fragments that are joined to one or more nucleic acid adaptors by hybridization (e.g., with or without a primer extension reaction) or enzymatic ligation (e.g., a ligase reaction) to generate adaptor-fragment constructs. In some embodiments, one end or both ends of polynucleotide fragments can be joined to at least one type of adaptor. One or both ends of a polynucleotide fragment can be joined to at least one nucleic acid adaptor, including barcoded adaptors, sequencing primer adaptors, amplification primer adaptors, universal adaptors, blocking oligonucleotide adaptors and/or others.

In some embodiments, an adaptor can include nucleotide sequences that are complementary to sequencing primers (e.g., P1, P2 and/or A), amplification primers, universal sequences and/or barcode sequences. For example, released mate pair constructs can be joined at each end to a different sequencing adaptor to prepare a nucleic acid library for sequencing with SOLiD™ sequencing reactions (WO 2006/084131) or sequencing with ion-sensitive sequencing reactions (e.g., Ion Torrent PGM™ and Proton™ sequencers from Life Technologies Corporation, see for example U.S. Patent Publication Nos. 2010/0301398, 2010/0300895, 2010/0300559, 2010/0197507, 2010/0137143, 2009/0127589; and 2009/0026082, which are incorporated by reference in their entireties).

Barcoded Adaptor Sequences

In some embodiments, the present teachings are directed to methods for preparing a library of polynucleotide constructs which can include joining at least one end of a plurality of polynucleotide fragments to an adaptor having a barcode sequence. A barcode sequence can be a selected sequence of nucleotide bases (e.g. adenine, guanine, cytosine, thymine, uracil, inosine, or analogs thereof) in the polynucleotide strand that serves to identify the polynucleotide strand and/or distinguish it from other polynucleotide strands (e.g. those containing a different target sequence of interest). In some embodiments, a barcode adaptor can include a unique identification sequence (e.g., barcode sequence). A barcode sequence can be used for various purposes, such as tracking, sorting, and/or identifying the samples.

Because different barcode sequences can be associated with different polynucleotide strands, these barcode sequences may be useful in multiplexed sequencing of different samples. In some embodiments, a barcode adaptor can be used for constructing multiplex nucleic acid libraries. In some embodiments, one or more barcode sequences can allow identification of a particular adaptor among a mixture of different adaptors having different barcodes sequences. For example, a mixture can include 2, 3, 4, 5, 6, 7-10, 10-50, 50-100, 100-200, 200-500, 500-1000, or more different adaptors having unique barcode sequences. Examples of various adaptors having barcode sequences can be found in PCT/US2011/054053 which is incorporated by reference in its entirety.

In various high throughput DNA sequencing technologies (such as sequencing-by-synthesis) it is desirable to permit sequencing of different samples that are pooled together for simultaneous analysis (sometimes referred to as multiplexed sequencing).

When carrying out multiplexed sequencing, it is generally desirable to identify the origin of each sample, and this may require that the sequencing data be deconvolved for each sample. In particular, it can be desirable to uniquely identify the source of the sequence data derived from a multiplex sample (for example, to identify a particular nucleic acid species associated with different sample populations). One approach to facilitate sample identification is the use of unique nucleic acid identifier sequences (barcode adaptors) that are embedded within the sample construct so that sequencing data can be correctly identified or associated with its source sample.

System and Methods for Identifying Sequence Variation

Identification of sequence variants including single nucleotide polymorphism (SNPs), insertions, and deletions is an important application of next generation sequencing technologies.

Figure 3:
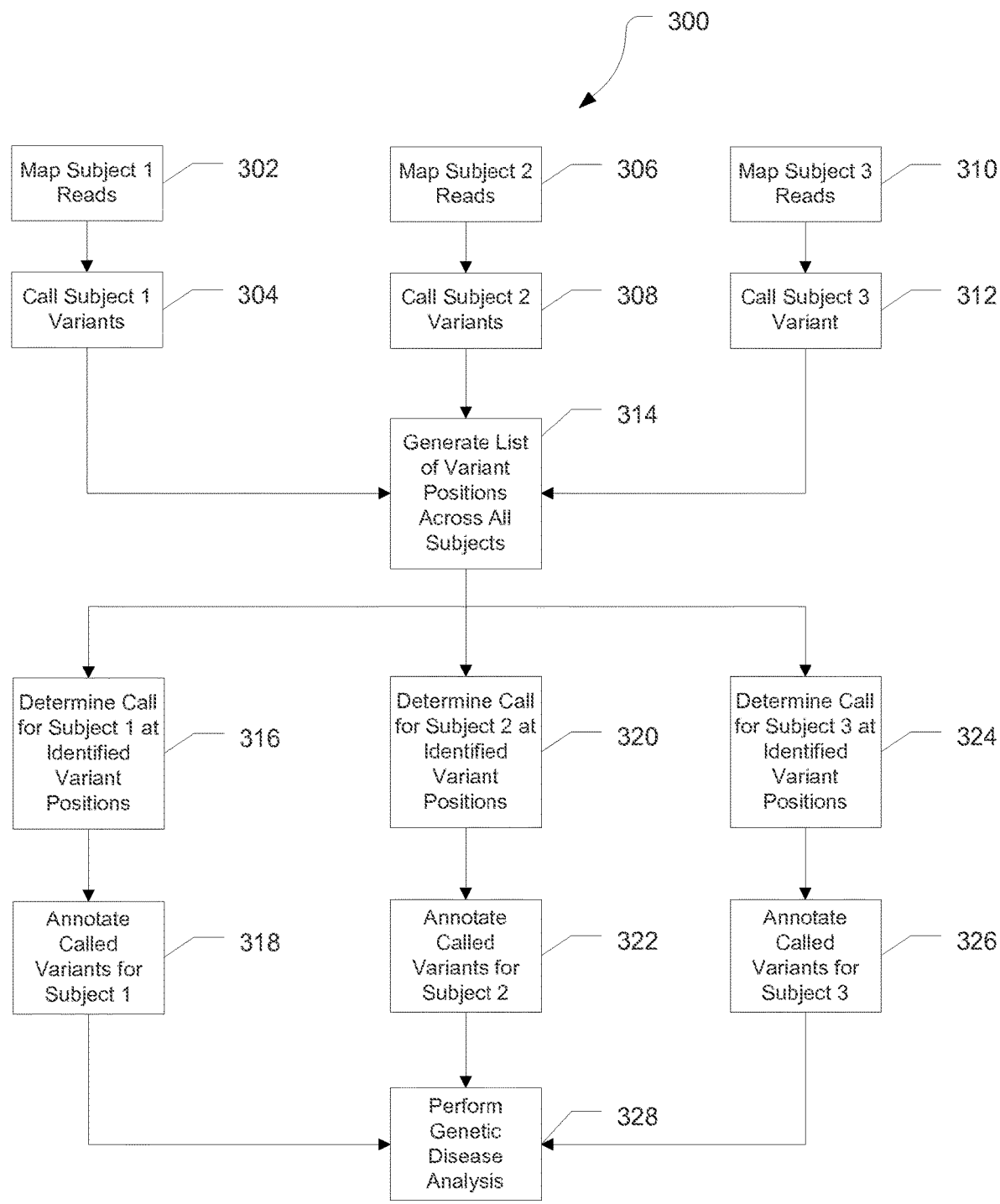
FIG. 3 is a flow diagram illustrating an exemplary method of calling variants, in accordance with various embodiments.

FIG. 3 is an exemplary flow diagram showing a method 300 for identifying variants in nucleic acid sequence reads from multiple related individuals, in accordance with various embodiments. In various embodiments, the subjects can be sequenced substantially simultaneously, such as by using unique barcode sequences for the individual samples and multiplexing the samples during a sequencing run. In other embodiments, the subjects can be sequenced individually. In yet other embodiments, a subset of the subjects can be sequenced substantially simultaneously while other subjects may be sequenced individually or as part of another multiplexed sequencing run.

At 302, reads from a first subject can be mapped to a reference genome. Various algorithms are known in the art for mapping reads to a reference genome. In particular embodiments, the mapping to the reference genome can be performed in base space after the reads are converted from flow space to base space.

At 304, the mapped reads can be used to identify variant positions for the first subject. Variant positions are positions where the reads that map to a position have a sequence that does not match the reference sequence and there is sufficient evidence among the reads to support a hypothesis that the variant exists in the genetic sequence of the subject.

At 306, reads from a second subject can be mapped to a reference genome, and at 308, the mapped reads for the second subject can be used to identify variant positions for the second subject. Similarly, at 310, reads from a third subject can be mapped to a reference genome, and at 312, the mapped reads for the third subject can be used to identify variant positions for the third subject.

In various embodiments, the first, second, and third subjects can be related, such as a mother, a father, and a child. In various embodiments, comparisons can be made of two subjects, such as a child and one parent or an affected individual and an unaffected sibling. In other embodiments, comparisons can be made among more than three individuals. For example, various combinations between parents, affected children, and unaffected children can be compared. In further embodiments, relationships can be defined by more complex genealogical trees, such as multigenerational family trees and comparisons can be made among affected and unaffected individuals within an extended family.

At 314, a list of variant positions can be generated from the variants positions identified for the first, second, and third individuals. That is, the list contains variant positions identified in at least one of the first, second, and third individuals.

At 316, a call for the first subject can be made for the identified variant positions from the list of variant positions. The call can indicate the genetic sequence of the individual is different from the reference sequence or the same as the reference sequence at the variant position. In various embodiments, the call may identify the position as ambiguous when there is some evidence of a variant, but the evidence is insufficient to confidently call the position as a variant.

At 318, the called variants for the first subject can be annotated with functional and non-functional information. For example, variants can be annotated based on the type of mutations, such as a missense variant, an indel, a splice variant, a stop loss, a stop gain, a homologous variant, and the like. Additionally, variants can be annotated with information as to which protein the variant may affect, which pathway the protein is involved in, known disease states related to the protein or the variant position, and the like.

At 320 and 324, a call for the second and third subjects, respectively, can be made for the identified variant positions from the list of variant positions. At 322 and 326, the called variants for the second and third subjects, respectively, can be annotated with functional and non-functional information.

At 328, the variant positions and the calls can be used to perform a genetic disease analysis. During the genetic disease analysis comparisons can be made between the calls for the subjects to identify variants or combinations of variants that are unique to an affected individual or a group of affected individuals. For example, genetic disease analysis can identify de novo variants that are found in a child but not in either parent, such as spontaneous mutations, recessive alleles, such as a homozygous position in a child where the parents are heterozygous, compound heterozygous variants, where multiple variants occur within a region coding for a protein and the like.

Figure 4:
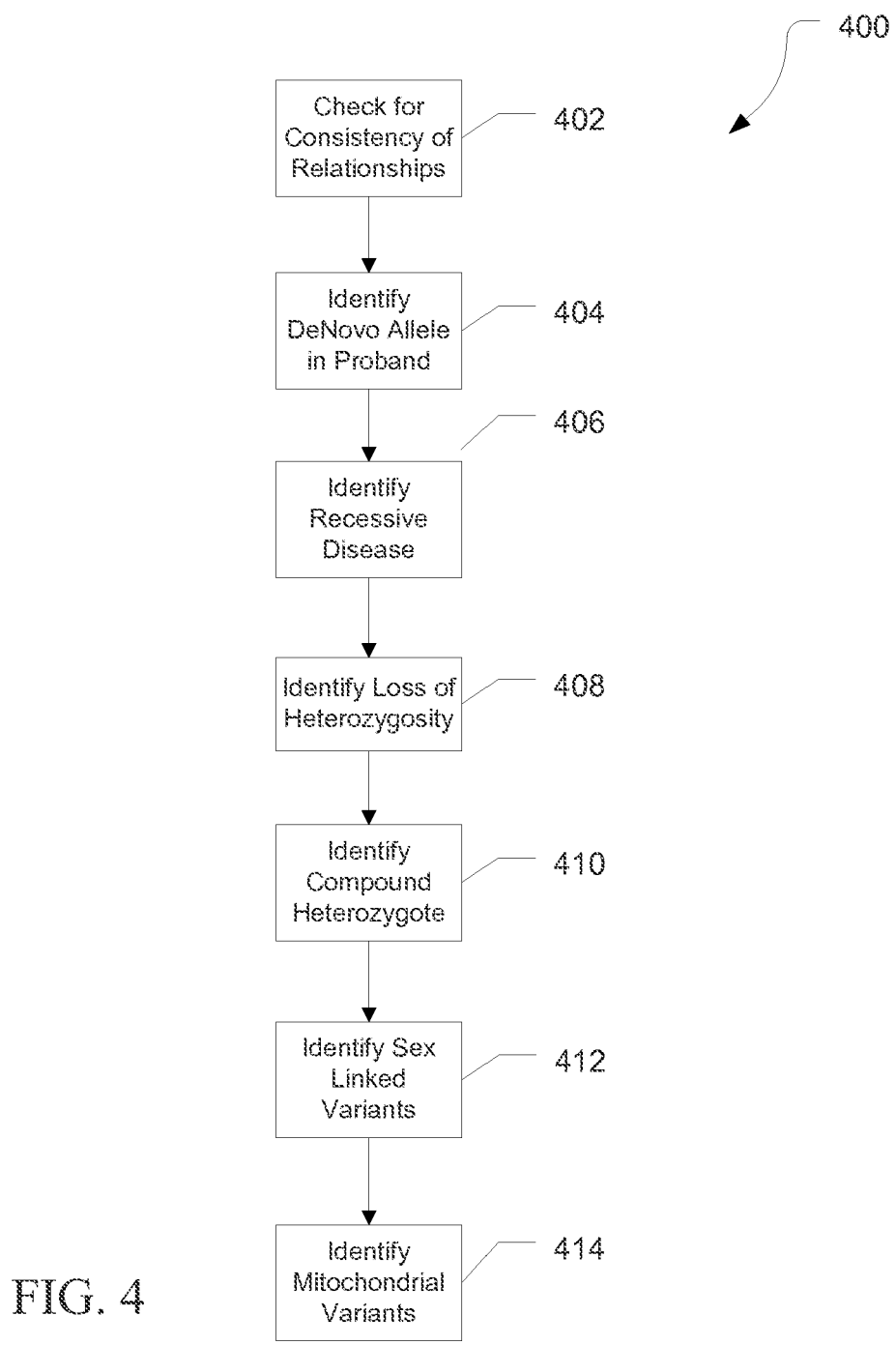
FIG. 4 is a flow diagram illustrating an exemplary method of identifying variants associated with genetic disease, in accordance with various embodiments.

FIG. 4 is an exemplary flow diagram showing a method 400 for identifying variants in nucleic acid sequence reads from multiple related individuals, in accordance with various embodiments.

At 402, a check for consistency of subject identification can be performed. In various embodiments, checks can be performed to ensure that the sequence information is consistent with the sex of a subject or the relationship between subjects. For example, consistency of the genetic data with the identified sex of a sample can be verified by looking at the presence or absence of Y chromosome sequences or the presence of multiple alleles for the X chromosome.

Similarly, the defined relationship between samples can be checked by looking for signs of inheritance of alleles from both parents by a child. In particular embodiments, variant positions can be checked for consistency, and inconsistent positions can be marked as inconsistent. Table 1 provides a non-exhaustive list of examples.

TABLE 1

| Child | Mother | Father | Inconsistent |
|-------|--------|--------|--------------|
| AA    | AT     | AT     | No           |
| TT    | AT     | AT     | No           |
| AT    | AT     | AT     | No           |
| AT    | AA     | TT     | No           |
| AA    | AA     | AA     | No           |

TABLE 1-continued

| Child | Mother | Father | Inconsistent |
|-------|--------|--------|--------------|
| AA | TT | AT | Yes |
| AA | TT | AA | Yes |
| AT | AA | AA | Yes |
| AC | TT | AT | Yes |

In various embodiments, a check for misidentification of a father, mother, child relationship can be performed by taking a ratio of positions that have been identified as inconsistent (b) to the total number of positions (a). If the ratio exceeds a threshold (b/a>Tp), then the relationship can be marked as potentially misidentified. By way of an example, the threshold may be set to 0.20 or may be configurable by the user.

Further, a check for misidentification of paternity can be checked by taking a ratio of positions that have been identified as inconsistent with the father (c) to the total number of positions (a). A position can be marked as inconstant with the father when the alleles in the child are not found in the father. If the ratio exceeds a threshold (c/a>Tp), then the relationship can be marked as potentially misidentified.

Similarly, misidentification of maternity can be checked by taking a ratio of positions that have been identified as inconsistent with the mother (d) to the total number of positions (a). A position can be marked as inconstant with the father when the alleles in the child are not found in the mother. If the ratio exceeds a threshold (d/a>Tp), then the relationship can be marked as potentially misidentified.

In various embodiments, checks of the identification of the X chromosome, the Y chromosome, or the mitochondrial chromosome, can be performed. In instances where there are no variant positions found for the X, Y, or mitochondrial chromosome in any of the samples, potential misidentification of the X, Y, or mitochondrial chromosomes may be indicated.

At 404, de novo alleles in a proband can be identified. The proband can be a target individual, such as an individual affected by a phenotype or genetic disease. In various embodiments, the proband can be the child of the child-mother-father relationship. De novo alleles can include positions where neither parent matches at least one allele of the proband. For example, if the proband is heterozygous AC at a position where neither parent has C at the position, such as, for example, the parents are AA and TT, the C is a de novo allele at the position. The de novo allele can be classified as reference when the de novo allele matches the reference genome where neither parent matches the reference genome, or non reference when the de novo allele is different from the reference genome. In various embodiments, the de novo allele can represent a spontaneous mutation that is unique to the proband. Further, a non reference de novo allele may give rise to a phenotype or genetic disease that is present in the proband but not in the parents. In various embodiments, classifying a position as a de novo allele can require sufficient coverage, such as 10×, of the position in the parents. Additionally, the coverage limit can be configurable by the user.

At 406, recessive traits or diseases can be identified. A position can be identified as potentially giving rise to a recessive trait or disease when the child who is recessive at the position exhibits the trait or is affected by the disease and the parents are heterozygous at the position and unaffected. Recessive positions may be of particular interest when the variant has a functional classification of missense, indel, splice variant, stop loss, or stop gain, as these types of mutations can result in a loss of function or a reduced function for a protein encoded by a gene containing the recessive variant.

At 408, loss of heterozygosity at a position can be identified. Loss of heterozygosity at a position can be the result of a deletion or chromosomal rearrangement and can affect protein function, regulation, etc. Loss of heterozygosity can be identified when the proband has a high percentage of homozygous positions within a region of the genetic sequence where the parents exhibit multiple variants. In various embodiments, loss of heterozygosity can be identified using a rolling average of the percentage of variants that are homozygous, using a percentage of variants that are homozygous for a fixed window size, using a rolling average of a percentage of consecutive variants that are heterozygous. In various embodiments, candidate regions can be identified by scanning across the genetic information of the child. When a region is found that may be a loss of heterozygosity in the child, the genetic information from the parents can be compared to determine if the parents exhibit a similar lack of heterozygosity. When neither parent has a similar loss of heterozygosity, it may indicate a spontaneous deletion or rearrangement for the child that may give rise to a disease that doesn't affect either parent. Alternatively, when one parent exhibits a similar loss of heterozygosity, it may indicate a chromosomal alteration that was inherited from the parent, which may be unrelated to the disease or trait when the parent is unaffected.

At 410, compound heterozygote can be identified. A compound heterozygote is multiple variants, such as missense, indel, splice, stop loss, or stop gain variants, within a single gene. Trans-phased compound heterozygotes, where one variant allele is inherited from one parent, and another variant allele is inherited from the other parent, can be of particular interest. Trans-phased compound heterozygotes may result in a child exhibiting a disease or trait as a result of having two misfunctional copies of a gene, without being homozygous for a recessive misfunctional variant. Compound heterozygotes can be identified by looking at combinations of heterozygous positions within a gene.

At 412, sex linked variants can be identified. Sex linked variants can be variants found in the X or Y chromosomes of a male child. The child inherits the Y chromosome from the father and the X chromosome from the mother and is hemizygous (has only one copy) for genetic information from both the X and Y chromosomes. When neither the mother or father exhibit a trait or are affected by a genetic disease, variants of the X chromosome where the father is reference and the mother is heterozygous may be of particular interest. Also of interest are variants on either the X or Y chromosome that are unique to the child and not found in either the mother or father. When the father is affected, variants on the Y chromosome can be of interest.

At 414, mitochondrial variants can be identified. Generally, the mitochondrial genome is inherited from the mother. Further, as a cell contains multiple mitochondria, diseases can be related to a number of mitochondria containing a misfunctional mutation (misssense, splice, indel, stop loss, stop gain). Mitochondrial variants potentially related to a genetic can be identified by identifying low to moderate frequency variants in the child that are not present or present at a lower frequency in the mother.

In various embodiments, genetic trait/disease analysis can be performed on a trio of mother, father, and child (proband). In particular embodiments, the child can be affected and the parents can be unaffected. The analysis can be used to identify variant classes that are present in the child and absent in the parents as potentially relating to the trait/disease. In particular embodiments, the child and one parent can be affected and the other parent can be unaffected and the analysis can be used to identify variant classes that are present in the child and affected parent, but are absent in the unaffected parent as potentially relating to the trait/disease.

In various embodiments, genetic information may be limited to a single parent when genetic material from both parents is unavailable. The analysis can identify variant classes that are present in the child and absent in the available parent as potentially related to the trait/disease present in the child. However, the number of false positives, variant classes present in the child, not present in the parent, but unrelated to the trait/disease, may be higher as alleles from another unaffected parent may be more difficult to eliminate without the genetic information from the other parent.

In various embodiments, genetic trait/disease analysis can be performed on a family unit including mother, father, and siblings. The siblings may include affected and unaffected siblings. In various embodiments, genetic trait/disease analysis can be performed on extended families and can include mother, father, siblings, grandparents, cousins, and more distantly related individuals. Extended family analysis can include various combinations of affected and unaffected individuals. The analysis can be used to identify variant classes that are common to the affected individuals and are absent in unaffected individuals as potentially relating to the trait/disease.

Figure 5:
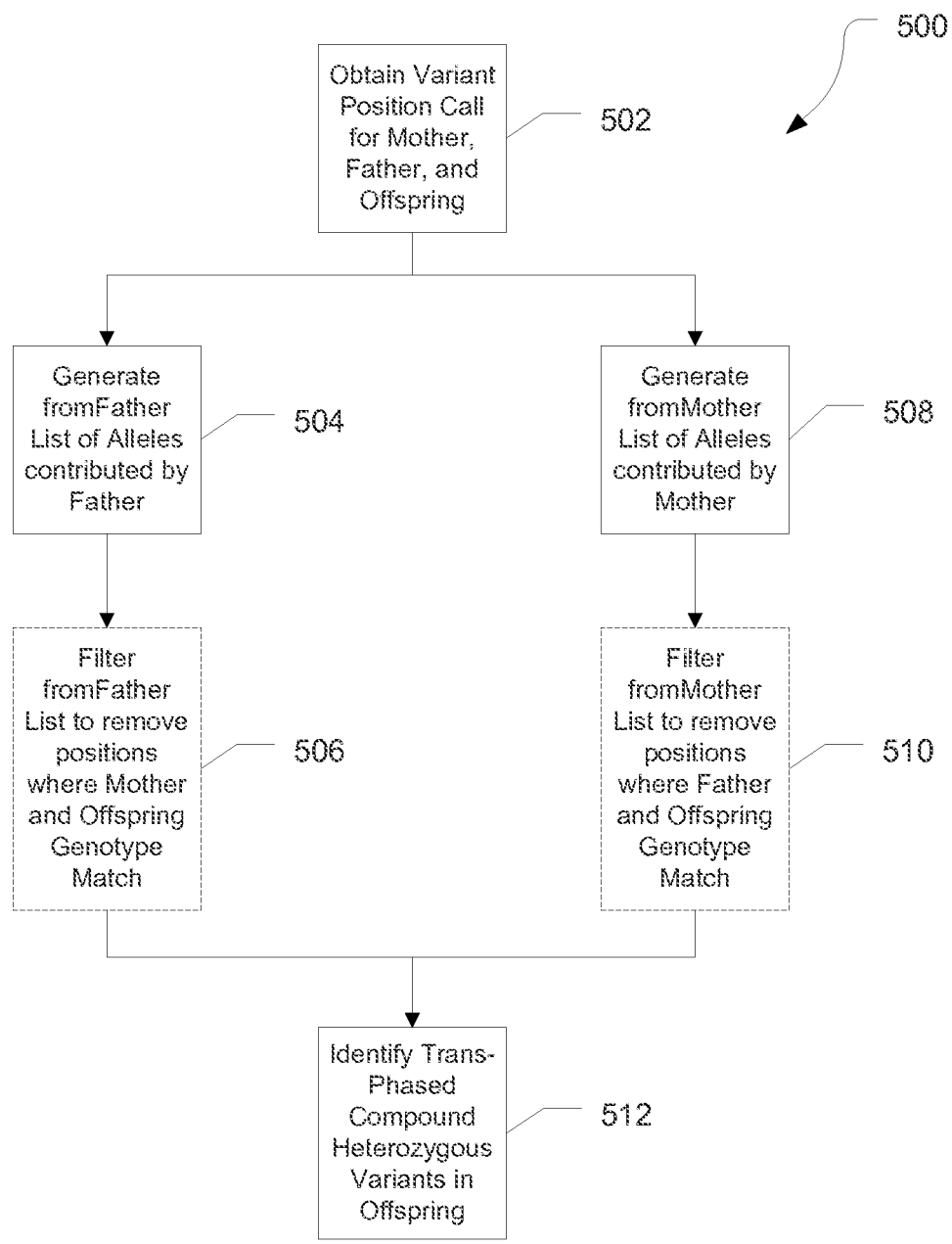
FIG. 5 is a flow diagram illustrating an exemplary method of identifying trans-phased compound heterozygous variants, in accordance with various embodiments.

FIG. 5 is exemplary flow diagram showing a method 500 for identifying trans-phased compound heterozygous variants, in accordance with various embodiments.

In various embodiments, a compound heterozygote can refer to a genetic condition in which alleles of a locus have mutations at a different nucleotide sites. A compound heterozygote individual may have two different pathenogenic mutations in the same gene that together are sufficient to manifest a recessive phenotype. That is, the individual may inherit or otherwise have two defective copies of a gene where the defects are different, such as at two different locations within the gene that would not be identified as a homozygous recessive variant.

Figure 7:
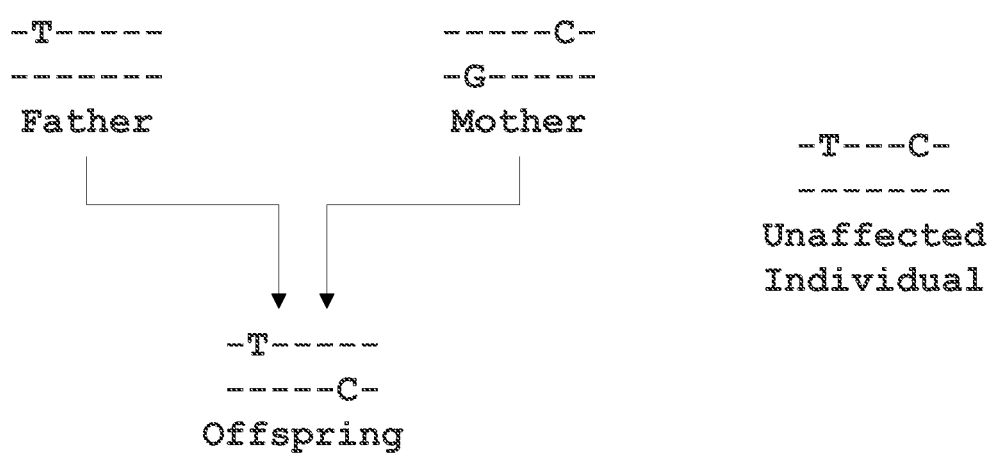
FIG. 7 is a diagram illustrating a mother-father-offspring trio where the offspring is a trans-phased compound heterozygote, in accordance with various embodiments.

By way of an example, referring to FIG. 7, the Father can have a reference allele and a non-reference allele with a variant, T, at a first position. The mother can have a non-reference allele with a variant, G, at a first position, and a non-reference allele with a variant, C, at a second position. The offspring can be a trans-phased compound heterozygote, having inherited the non-reference allele with a T at the first position from the Father and the non-reference allele with a C at the second position from the mother. In a particular example, where the T and C are loss-of-function mutations and the G is a homologous mutation, both the mother and father can have a functional copy of the gene, the reference allele for the father and the allele with the G for the mother, while the offspring can have two non-functional copies of the gene.

In various embodiments, next generation sequencing of the may not provide sufficient information to distinguish a trans-phased compound heterozygote, such as the offspring, from a cis-phased compound heterozygote, such as the unaffected individual. For example, the first and second positions may be sufficiently far apart that no single reads spans both positions to identify that the variants are on the same copy of the gene or different copies of the gene. The analysis can be further complicated by not knowing if a specific allele at a position is inherited from the mother or the father when both parents have the same allele at the position.

At 502, calls are obtained for variant positions for each of the mother, father, and offspring. In various embodiments, at each position where a variant is identified in any of the mother, father, or offspring, a call is made for each individual to determine the genotype at that position. The genotype may include alleles that match the reference or non-reference alleles.

At 504, a list of variants that may have been inherited from the father is generated. In various embodiments, the list includes variants where one of the two variants of the offspring has a non-reference allele that is present in the father's genotype where the other allele is present in the mother's genotype.

At 506, the list of variants from the father can be filtered to remove variants where the offspring genotype matches the genotype of the mother. In various embodiments, the mother can be a non-affected individual and the offspring can be an affected individual. In that situation, combining a position where the mother and offspring match with a non-reference allele from the mother is unlikely to identify a compound heterozygote that is causative of the phenotype exhibited only by the offspring.

At 508, a list of variants that may have been inherited from the mother is generated, and at 510, the list of variants from the mother can be filtered to remove variants where the offspring genotype matches the genotype of the father.

At 512, trans-phased compound heterozygote variants can be identified by combining positions in the list of variants from the father with positions in the list of variants from the mother. In various embodiments, this can identify combinations of positions where a non-reference allele is contributed from the father with positions where a non-reference allele is contributed from the mother. In particular embodiments, trans-phased compound heterozygotes can also be identified at a single position where the father and mother each contribute a different non-reference allele.

Figure 8:
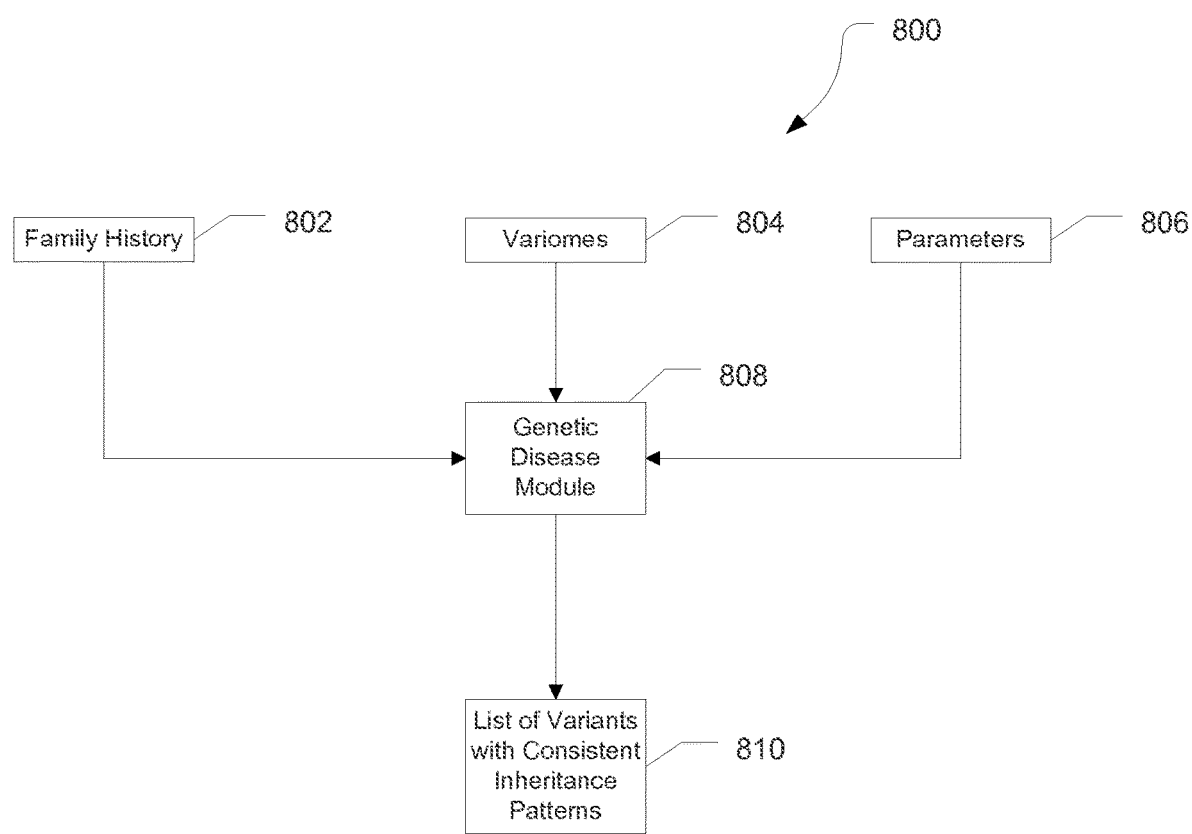
FIG. 8 is flow diagram illustrating an exemplary method of identifying variants associated with a phenotype, in accordance with various embodiments.

FIG. 8 is exemplary flow diagram showing a method 800 for identifying variants associated with a phenotype, in accordance with various embodiments. At 802, a family history can be provided. The history can include, for an individual, the pedigree relationship to the proband, an indication of the mother and father of the individual, if known, and an indication as to if the individual is affected or unaffected.

At 804, a set of variomes can be provided along with a map that assigns each variome to exactly one individual in the family. In various embodiments, the set of variomes will include a variome assigned to the proband and variomes assigned to at least a subset of other family members. In various embodiments, variomes have a genotype at all positions for which the proband variome has a genotype call can be considered. The genotype call can be a variant pair, a reference pair, or a "no-call". At 806, a set of parameters that defines what it means for an allele to be deleterious can be provided.

At 808, the genetic disease module can perform and analysis of the data from 802, 804, and 806, and identify inheritance patterns that are consistent with the input data, which can be provided at 810.

In various embodiments, a variant at a position can be marked as consistent with a pattern of inheritance if (a) the genotype at the position for each individual is consistent with Mendelian inheritance from its parents, and (b) the genotype at the position for each individual is consistent with its status of affected or unaffected under inheritance pattern and the assumption of 100% penetrance. The patterns of inheritance can include autosomal recessive, autosomal dominant, x-linked recessive, x-linked dominant, or mitochondrial.

In various embodiments, to determine if a genotype is consistent with Mendelian inheritance, we need to know if a given allele could have come from a parent, given the information available from the Input. An allele of a genotype for a position for an individual could have come from a given parent if (a) the allele is present in that parent's genotype at the position, (b) the parent's genotype at the position is a "no call", (c) the parent does not have a genotype at the position, or (d) the parent is unknown. The patent may not have a genotype at the position when the parent is identified in the family history at 802, but does not have a corresponding variome at 804. The parent can be unknown when the parent is not identified in the family history at 802.

In various embodiments, to determine if a genotype is consistent with autosomal Mendelian inheritance if (a) the genotype appears on an autosome, (b) one of its alleles could have come from its father, and (c) the other of its alleles could have come from its mother. In various embodiments, to determine if a genotype is consistent with X-linked Mendelian inheritance if (1) the genotype appears on chromosome X, (2) the individual is female and (a) one of its alleles could have come from its father, and (b) the other of its alleles could have come from its mother, and (3) if the individual is male and its allele appears in the mother's genotype at the position. In various embodiments, to determine if a genotype is consistent with mitochondrial Mendelian inheritance if (1) the genotype appears in the mitochondrial genome, and (2) its allele could have come from its mother. In various embodiments, to determine if a genotype is consistent with Y-linked Mendelian inheritance if (a) the genotype appears on chromosome Y, (b) the individual is male, and (c) its allele could have come from its father.

In mammals, there are two subsequences of homology, PAR1 and PAR2, between the X and Y chromosomes. These pseudoautosomal regions segregate and recombine during male meiosis. Consequently, an allele in the PAR on the father's Y-chromosome can be passed to a daughter's X chromosome, and an allele in the PAR on the father's X-chromosome can be passed to a son's Y chromosome in a pseudoautosomal inheritance pattern. In various embodiments, to determine if a genotype is consistent with pseudoautosomal Mendelian inheritance if (1) the genotype appears in PAR1 or PAR2 on chromosome X or Y, (2) one of its alleles could have come from its father, and (b) the other of its alleles could have come from its mother.

An autosomal recessive inheritance pattern is indicative of the variant where a phenotype is expressed when an individual is homozygous for the corresponding allele. In various embodiments, the genotype of an affected individual can be consistent with autosomal recessive inheritance if (1) it is consistent with autosomal Mendelian inheritance, and (2) both of its alleles are deleterious. The genotype of an unaffected individual can be consistent with autosomal recessive inheritance if (1) it is consistent with autosomal Mendelian inheritance, and (2) at least one of the alleles is benign.

An autosomal dominant inheritance pattern is indicative of the variant where a phenotype is expressed when an individual has at least one copy of the corresponding allele.

In various embodiments, the genotype of an affected individual can be consistent with autosomal dominant inheritance if (1) it is consistent with autosomal Mendelian inheritance, (2) at least one of its alleles is deleterious, and (3) at least one of its parents is affected. In various embodiments, the genotype of an unaffected individual can be consistent with autosomal dominant inheritance if (1) it is consistent with autosomal Mendelian inheritance, and (2) both of its alleles are benign.

An X-linked recessive inheritance pattern is indicative of the variant where a phenotype is expressed when the corresponding allele is present for all X chromosomes for an individual. In various embodiments, the genotype of an affected individual can be consistent with X-linked recessive inheritance if (1) the genotype is consistent with X-linked Mendelian inheritance and (2) if the individual is male and his allele is deleterious, and (3) if the individual is female and both of her alleles are deleterious. In various embodiments, the genotype of an unaffected individual can be consistent with X-linked Recessive inheritance if (1) the genotype is consistent with X-linked Mendelian inheritance and (2) if the individual is male and his allele is benign, and (3) if the individual is female and at least one of her alleles is benign.

An X-linked dominant inheritance pattern is indicative of the variant where a phenotype is expressed when the corresponding allele is present for at least one X chromosome for an individual. In various embodiments, the genotype of an affected individual can be consistent with X-linked Dominant inheritance if (1) the genotype is consistent with X-linked Mendelian inheritance, (2) if the individual is male, his allele is deleterious and his mother is affected, and (3) if the individual is female, at least one of her alleles is deleterious and at least one of her parents is affected. In various embodiments, the genotype of an unaffected individual can be consistent with X-linked Dominant inheritance if (1) the genotype is consistent with X-linked Mendelian inheritance, and (2) if the individual is male and his allele is benign, and (3) if the individual is female and both of her alleles are benign.

A mitochondrial inheritance pattern is indicative of the variant where a phenotype is expressed when the corresponding allele is present in the mitochondrial genome for an individual. In various embodiments, the genotype of an affected individual can be consistent with mitochondrial inheritance if (1) it is consistent with mitochondrial Mendelian inheritance, (2) at least one of its alleles is deleterious, (3) that allele appears in the mother's genotype, and (4) the mother is affected. In various embodiments, the genotype of an unaffected individual can be consistent with mitochondrial inheritance if (1) it is consistent with mitochondrial Mendelian inheritance, (2) all of its alleles are benign, and (3) the mother is unaffected.

A Y-linked inheritance pattern is indicative of the variant where a phenotype is expressed when the corresponding allele is present on the Y chromosome for an individual. In various embodiments, the genotype of an affected individual can be consistent with Y-linked inheritance if (1) it is consistent with Y-linked Mendelian inheritance, (2) its allele is deleterious, (3) that allele appears in the father's genotype, and (4) its father is affected. In various embodiments, the genotype of an unaffected individual can be consistent with Y-linked inheritance if (1) it is consistent with Y-linked Mendelian inheritance, (2) its allele is benign, and (3) its father is unaffected.

A Pseudoautosomal Recessive inheritance pattern is indicative of the variant where a phenotype is expressed when an individual is homozygous for the corresponding allele in the pseudoautosomal regions. In various embodiments, the genotype of an affected individual can be consistent with pseudoautosomal recessive inheritance if (1) it is consistent with pseudoautosomal Mendelian inheritance, and (2) both of its alleles are deleterious. In various embodiments, the genotype of an unaffected individual can be consistent with pseudoautosomal recessive inheritance if (1) it is consistent with pseudoautosomal Mendelian inheritance, and (2) at least one of its alleles is benign.

A Pseudoautosomal Dominant inheritance pattern is indicative of the variant where a phenotype is expressed when an individual has at least one copy of the corresponding allele in the pseudoautosomal regions. In various embodiments, the genotype of an affected individual can be consistent with pseudoautosomal dominant inheritance if (1) it is consistent with pseudoautosomal Mendelian inheritance, (2) at least one of its alleles is deleterious, and (3) at least one of its parents is affected. In various embodiments, the genotype of an unaffected individual can be consistent with pseudoautosomal dominant inheritance if (1) it is consistent with pseudoautosomal Mendelian inheritance, and (2) both of its alleles are benign.

Figure 6:
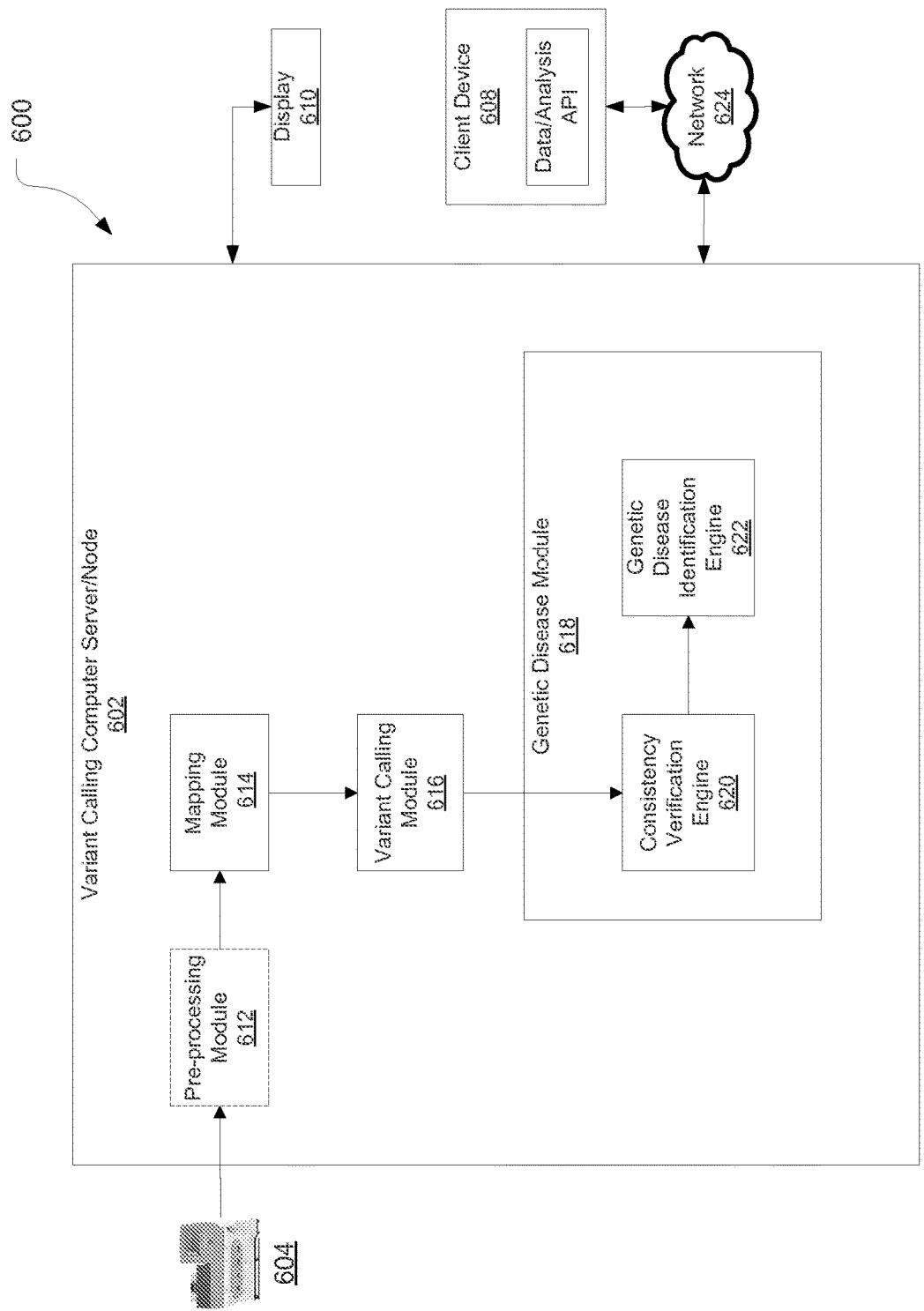
FIG. 6 is a schematic diagram of an exemplary variant calling system, in accordance with various embodiments.

FIG. 6 is a schematic diagram of a system for identifying variants, in accordance with various embodiments.

As depicted herein, variant analysis system 600 can include a nucleic acid sequence analysis device 604 (e.g., nucleic acid sequencer, real-time/digital/quantitative PCR instrument, microarray scanner, etc.), an analytics computing server/node/device 602, and a display 610 and/or a client device terminal 608.

In various embodiments, the analytics computing server/node/device 602 can be communicatively connected to the nucleic acid sequence analysis device 604, and client device terminal 608 via a network connection 624 that can be either a "hardwired" physical network connection (e.g., Internet, LAN, WAN, VPN, etc.) or a wireless network connection (e.g., Wi-Fi, WLAN, etc.).

In various embodiments, the analytics computing server/node/device 602 can be a workstation, mainframe computer, distributed computing node (part of a "cloud computing" or distributed networking system), personal computer, mobile device, etc. In various embodiments, the nucleic acid sequence analysis device 604 can be a nucleic acid sequencer, real-time/digital/quantitative PCR instrument, microarray scanner, etc. It should be understood, however, that the nucleic acid sequence analysis device 604 can essentially be any type of instrument that can generate nucleic acid sequence data from samples obtained from an individual.

The analytics computing server/node/device 602 can be configured to host an optional pre-processing module 612, a mapping module 614, a variant calling module 616, and a genetic disease module 618.

Pre-processing module 612 can be configured to receive from the nucleic acid sequence analysis device 604 and perform processing steps, such as conversion from flow space to base space, determining call quality values, preparing the read data for use by the mapping module 614, and the like.

The mapping module 614 can be configured to align (i.e., map) a nucleic acid sequence read to a reference sequence. Generally, the length of the sequence read is substantially less than the length of the reference sequence. In reference sequence mapping/alignment, sequence reads are assembled against an existing backbone sequence (e.g., reference sequence, etc.) to build a sequence that is similar but not necessarily identical to the backbone sequence. Once a backbone sequence is found for an organism, comparative sequencing or re-sequencing can be used to characterize the genetic diversity within the organism's species or between closely related species. In various embodiments, the reference sequence can be a whole/partial genome, whole/partial exome, etc.

In various embodiments, the sequence read and reference sequence can be represented as a sequence of nucleotide base symbols in base space. In various embodiments, the sequence read and reference sequence can be represented as one or more colors in color space. In various embodiments, the sequence read and reference sequence can be represented as nucleotide base symbols with signal or numerical quantitation components in flow space.

In various embodiments, the alignment of the sequence fragment and reference sequence can include a limited number of mismatches between the bases that comprise the sequence fragment and the bases that comprise the reference sequence. Generally, the sequence fragment can be aligned to a portion of the reference sequence in order to minimize the number of mismatches between the sequence fragment and the reference sequence.

The variant calling module 616 can be configured to identify differences between the mapped nucleic acid sequence reads and the reference sequence. In various embodiments, variant calling module 616 can be in communications with the mapping module 614. That is, the variant calling module 616 can request and receive data and information (through, e.g., data streams, data files, text files, etc.) from mapping module 614. In various embodiments, the variant calling module 616 can be configured to communicate variants called for a sample genome as a *.vcf, *.gff, or *.hdf data file. It should be understood, however, that the called variants can be communicated using any file format as long as the called variant information can be parsed and/or extracted for later processing/analysis.

The genetic disease module 618 can include a consistency verification engine 620, and a genetic disease identification engine 622. In various embodiments, genetic disease module 618 can be in communications with the variant calling module 616. That is, the genetic disease module 618 can request and receive data and information (through, e.g., data streams, data files, text files, etc.) from variant calling module 616.

The consistency verification engine 620 can be configured to receive variants from the variant calling module 616, and check for inconsistencies, such as checking for inconsistencies with the identified relationships between the subjects, or inconstancies with the identified sex of the subjects.

The genetic disease identification engine 622 can be configured to identify variants that may be associated with a genetic disease or a trait of the proband. In various embodiments, the analysis can include comparing genetic information from affected individuals and unaffected individuals to identify variants that are common among the affected individuals but not found in the unaffected individuals. The genetic disease identification engine 622 can compare the presence or absence of variants identified by the variant calling module 616 and can identify patterns of variants that are consistent with the genetic disease or trait.

Client device 608 can be a thin client or thick client computing device. In various embodiments, client terminal 608 can have a web browser (e.g., INTERNET EXPLORER™, FIREFOX™, SAFARI™, etc) that can be used to communicate information to and/or control the operation of the pre-processing module 612, mapping module 614, realignment engine 618, variant calling engine 620, and post processing engine 622 using a browser to control their function. For example, the client terminal 608 can be used to configure the operating parameters (e.g., match scoring parameters, annotations parameters, filtering parameters, data security and retention parameters, etc.) of the various modules, depending on the requirements of the particular application. Similarly, client terminal 608 can also be configure to display the results of the analysis performed by the variant calling module 616 and the nucleic acid sequencer 604.

It should be understood that the various data stores disclosed as part of system 600 can represent hardware-based storage devices (e.g., hard drive, flash memory, RAM, ROM, network attached storage, etc.) or instantiations of a database stored on a standalone or networked computing device(s).

It should also be appreciated that the various data stores and modules/engines shown as being part of the system 600 can be combined or collapsed into a single module/engine/data store, depending on the requirements of the particular application or system architecture. Moreover, in various embodiments, the system 600 can comprise additional modules, engines, components or data stores as needed by the particular application or system architecture.

In various embodiments, the system 600 can be configured to process the nucleic acid reads in color space. In various embodiments, system 600 can be configured to process the nucleic acid reads in base space. In various embodiments, system 600 can be configured to process the nucleic acid sequence reads in flow space. It should be understood, however, that the system 600 disclosed herein can process or analyze nucleic acid sequence data in any schema or format as long as the schema or format can convey the base identity and position of the nucleic acid sequence.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

What is claimed is:

1. A method for identifying variants associated with a genetic disease or genetic trait, the method comprising:

mapping, using a processor, a plurality of nucleic acid reads from a plurality of subjects to a reference genome, the subjects comprising a proband, a first biological relative of the proband, and a second biological relative of the proband, wherein the proband is affected by the genetic disease or genetic trait and comprises a phenotype associated with the genetic disease or genetic trait, and one or both of the first biological relative and the second biological relative are unaffected by the genetic disease or genetic trait;

based on the mapping, determining, using the processor, differences between the plurality of nucleic acid reads and the reference genome as variant positions in nucleic acid sequences of the proband, the first biological relative, and the second biological relative;

generating, using the processor, a first list of variants potentially inherited by the proband from the first biological relative and a second list of variants potentially inherited by the proband from the second biological relative at the determined variant positions;

filtering, using the processor, the first list of variants and the second list of variants to remove variants that do not contribute to compound heterozygous positions in the proband;

identifying, using the processor, one or more trans-phased compound heterozygous variants for the proband based on the filtering of the first and second lists; and outputting, using the processor, the one or more trans-phased compound heterozygous variants as a potential variant associated with the genetic disease or the genetic trait.

2. The method of claim 1, further comprising:
identifying, using the processor and based on the determining of the variant positions, a loss of heterozygosity, an increased frequency mitochondrial variant, or any combination thereof for the proband that are not found in the first biological relative and the second biological relative.

3. The method of claim 2, further comprising:
identifying, using the processor and based on the determining of the variant positions, a recessive variant, a de novo variant, a sex-linked variant, or any combination thereof for the proband that are not found in the first biological relative and the second biological relative.

4. The method of claim 1, wherein the first biological relative and the second biological relative respectively comprise a mother and a father of the proband.

5. The method of claim 1, further comprising annotating, using the processor, the variants with functional annotations.

6. The method of claim 1, wherein the plurality of nucleic acid reads are produced by sequencing polynucleotides of the subject, the polynucleotides being joined with differing barcodes to distinguish the subjects.

7. The method of claim 6, wherein the sequencing comprises sequencing by synthesis, detection of a released hydrogen ion, or both.

8. The method of claim 1, further comprising:
identifying, using the processor and based on the determining of the variant positions, one or more allelic variants for the proband.

9. The method of claim 8, wherein the one or more allelic variants comprises a recessive allele.

10. The method of claim 8, wherein the one or more allelic variants comprise first and second allelic variants of a common gene.

11. The method of claim 10, wherein the first biological relative has the first allelic variant and the second biological relative has the second allelic variant.

12. The method of claim 1, wherein:
filtering the first list of variants comprises removing first variants from the first list of variants for which the genotype of the proband matches the genotype of the second biological relative; and
filtering the second list of variants comprises removing second variants from the second list of variants for which the genotype of the proband matches the genotype of the first biological relative.

13. The method of claim 1, further comprising:
validating, using the processor, the first biological relative and the second biological relative have a parental relationship with the proband; and
outputting, using the processor, the parental relationship.

* * * * *